United States Patent
Afriat et al.

(10) Patent No.: US 6,656,487 B2
(45) Date of Patent: Dec. 2, 2003

(54) COMPOSITION CONTAINING FIBERS AND A DISPERSING COPOLYMER

(75) Inventors: Isabelle Afriat, Paris (FR); Florence Tournilhac, Paris (FR)

(73) Assignee: L'Oreal, Paris (FR)

(*) Notice: Subject to any disclaimer, the term of this patent is extended or adjusted under 35 U.S.C. 154(b) by 26 days.

(21) Appl. No.: 09/987,877

(22) Filed: Nov. 16, 2001

(65) Prior Publication Data

US 2002/0142014 A1 Oct. 3, 2002

(30) Foreign Application Priority Data

Dec. 5, 2000 (FR) .............................. 00 15741

(51) Int. Cl.⁷ .............................. A61K 7/00; A61K 9/14; A61K 31/08; A61K 31/74
(52) U.S. Cl. ................. 424/401; 424/78.02; 424/78.08; 424/484; 424/486; 424/488; 514/772.3; 514/844; 514/845; 514/846; 514/847; 514/848
(58) Field of Search ................. 424/401, 484, 424/488, 486, 78.02, 78.08; 514/772.3, 844, 845, 846, 847, 848

(56) References Cited

U.S. PATENT DOCUMENTS

| 5,935,559 | A  |   | 8/1999  | Afriat et al.            |
| 5,965,146 | A  |   | 10/1999 | Franzke et al.           |
| 6,239,174 | B1 |   | 5/2001  | Afriat et al.            |
| 6,331,306 | B1 |   | 12/2001 | Afriat et al.            |
| 6,342,237 | B1 | * | 1/2002  | Bara ............. 424/401 |
| 6,524,598 | B2 | * | 2/2003  | Sunkel et al. ...... 424/401 |

* cited by examiner

*Primary Examiner*—Shelley A. Dodson
(74) *Attorney, Agent, or Firm*—Oblon, Spivak, McClelland, Maier & Neustadt, P.C.

(57) ABSTRACT

The invention relates to a composition containing fibers and a copolymer comprising carboxylate groups and polydimethylsiloxane groups. The composition according to the invention may especially constitute a care or make-up composition for keratin materials such as the skin, including the scalp, the lips of the face and integuments, for instance the eyelashes, the eyebrows, the nails and the hair. The invention also relates to the use of a copolymer comprising carboxylate groups and polydimethylsiloxane groups in a composition containing fibers to ensure a homogeneous dispersion of the fibers in the composition and to stabilize the composition.

45 Claims, No Drawings

COMPOSITION CONTAINING FIBERS AND A DISPERSING COPOLYMER

BACKGROUND OF THE INVENTION

1. Field of the Invention

The present invention relates to a composition, preferably a composition suitable for topical application, containing fibers and a copolymer. The copolymer preferably comprises carboxylate groups and polydimethylsiloxane groups. The invention also relates to the manufacture and use of such compositions, for example in cosmetics and dermatology, and in particular to care for, treat or make up keratin materials such as the skin, including the scalp, the lips of the face and integuments, for instance the eyelashes, the eyebrows, the nails and the hair. The present invention also relates to the use of a copolymer comprising carboxylate groups and polydimethylsiloxane groups, in a composition containing fibers, as a dispersant and especially for ensuring a homogeneous dispersion of the fibers in the composition, to stabilize the composition, and to obtain a homogenous deposit of the composition on keratin materials.

2. Discussion of the Background

It is known practice to incorporate fibers into cosmetic compositions. Thus, document JP07-196 440 describes cosmetic composition containing short polyamide fibers, such as those giving a velvety feel and good cosmetic staying power. Moreover, in the field of skin make-up, it is known practice to use fibers in make-up products, especially for their lengthening effects in mascaras (see JP-A-57/158 714), their "textile" feel (see JP-A-7/196 440), their fabric effect or their moisturizing properties in lipsticks (see document U.S. Pat. No. 5,498,407) or to improve the contours of lipsticks on the edges of the lips (see document EP-A-0 106 762).

Unfortunately, it is difficult to disperse fibers in compositions for topical application homogeneously and without forming lumps, especially when these compositions are in the form of emulsions, and this heterogeneity of the dispersion generally gives heterogeneity when the composition is applied to the skin, and, when it is a coloured composition and in particular a make-up, it gives a non-uniform and unattractive make-up effect. In addition, this difficulty in dispersion leads to unstable compositions that are thus difficult to commercialize.

There is thus a need for a composition for topical application, and especially in the form of an emulsion, containing fibers, which does not have the above drawbacks, that is to say which has good stability and which gives a homogeneous and attractive care or make-up effect.

SUMMARY OF THE INVENTION

One subject of the invention is a composition, preferably for caring for and/or treating and/or making up keratin materials, which overcomes these drawbacks. Surprisingly, the Inventors have found that the use of a copolymer comprising carboxylate groups and polydimethylsiloxane groups provides a composition having very good stability and good cosmetic properties.

The invention applies not only to care, treatment and/or make-up products for the skin, including the scalp, and not only the skin of the human face but also of the body, and of the lips of the face, but also to make-up products for integuments, for instance the eyelashes, the eyebrows and the nails, and to care and/or treatment products for the hair.

The preparation and use of these compositions also makes up a part of the invention, as does the use of the invention copolymer to disperse and stabilize fibers in compositions.

DETAILED DESCRIPTION OF THE INVENTION

The invention composition, while not limited in form, is preferably one for topical application, preferably comprising a physiologically acceptable medium. In all cases, the invention composition comprises fibers and at least one copolymer comprising carboxylate groups and polydimethylsiloxane groups.

The expression "topical application" means herein an external application to keratin materials, which include the skin, the scalp, the eyelashes, the eyebrows, the nails, mucous membranes and the hair.

The invention composition preferably has a pleasant softness when applied to keratin materials and especially to the skin, and it preferably has good cosmetic staying power. In addition, the copolymer used in the composition of the invention allows the fibers to be dispersed homogeneously and ensures that the composition is stable over time. Moreover, it allows a more homogeneous deposit of the composition to be obtained on the keratin materials and especially on the skin, the scalp, the eyelashes, the eyebrows, the nails, mucous membranes and the hair.

Another subject of the invention is the use of a copolymer comprising carboxylate groups and polydimethylsiloxane groups in a composition containing fibers to ensure a homogeneous dispersion of the fibers in the composition and/or to stabilize the said composition.

Another subject of the invention is the use of a copolymer comprising carboxylate groups and polydimethylsiloxane groups, in a composition containing fibers, as a dispersant.

Another subject of the invention is the cosmetic use of a copolymer comprising carboxylate groups and polydimethylsiloxane groups, in a cosmetic composition containing fibers, to obtain a homogeneous deposit of the said composition on keratin materials.

The preparation of the invention compositions also makes up a part of the invention, including the mixing together of the copolymer and fibers, where "mixing together" includes all orders of addition of copolymer, fibers, and any and all other ingredients if present. Direct contact of copolymer and fiber is not required, as long as all components form one composition.

In the present patent application the term "fiber" should be understood as meaning an object of length L and diameter D such that L is greater than D, D being the diameter of the circle in which the cross section of the fiber is inscribed. Preferably, the ratio L/D (or shape factor) is chosen to be within the range from 3.5 to 2,500, preferably from 5 to 500 and better still from 5 to 150.

The fibers which may be used in the composition of the invention are not limited and include hydrophilic and hydrophobic fibers, of synthetic or natural, mineral or organic origin. These fibers may be in unit form or organized, for example into bundles. They may have any shape or morphology and preferably have a circular or polygonal (e.g., square, hexagonal or octagonal) cross section depending on the specific application envisaged. Preferably, their ends are blunt and/or polished to avoid injury. They may be multilobal and especially trilobal.

In a preferred embodiment, the fibers may have a length (L) ranging from 1 μm (0.001 mm) to 10 mm and more preferably from 0.1 µm to 5 mm. Their cross section may preferably be within a circle of diameter (D) ranging from 1 nm (0.001 µm) to 100 µm, more preferably ranging from 1 nm (0.001 µm) to 50 µm and better still from 5 µm to 40 µm.

The yarn count of the fibers is often given in denier or decitex. The denier is the weight in grams per 9 km of yarn. While not limited, preferably the fibers according to the invention have a yarn count ranging from 0.15 to 30 denier, and better still from 0.18 to 18 denier.

The shape factor, the yarn count and the morphology of the fibers are the three important factors for defining a fiber.

The fibers useful herein include those used in the manufacture of textiles, and in particular silk fiber, cotton fiber, cork fiber, sugar cane fiber, wool fiber, flax fiber, cellulose fiber extracted in particular from wood, from plants or from algae, polyamide (Nylon®) fiber, modified cellulose fiber (rayon fiber, viscose fiber, acetate fiber, in particular rayon acetate fiber), poly(p-phenyleneterephthalamide) fiber, in particular Kevlar® fiber, acrylic fiber, in particular polymethyl methacrylate fiber or poly(2-hydroxyethyl methacrylate) fiber, polyolefin fiber and in particular polyethylene or polypropylene fiber, glass fiber, silica fiber, aramide fiber, carbon fiber, in particular in graphite form, Teflon fiber, insoluble collagen fiber, polyester fiber, polyvinyl chloride fiber or polyvinylidene chloride fiber, polyvinyl alcohol fiber, polyacrylonitrile fiber, chitosan fiber, polyurethane fiber, polyethylene phthalate fiber, and fibers formed from a mixture of polymers such as those mentioned above, for instance polyamide/polyester fibers.

Resorbable synthetic fibers used in surgery can also be used herein, for instance the fibers prepared from glycolic acid and caprolactone (Monocryl® from Johnson & Johnson); resorbable synthetic fibers of the type which is a copolymer of lactic acid and of glycolic acid (Vicryl® from Johnson & Johnson); polyterephthalic ester fibers (Ethibond® from Johnson & Johnson) and stainless steel threads (Acier® from Johnson & Johnson).

Moreover, the fibers useful herein may be treated or untreated at the surface, and coated or uncoated, or both treated and coated. Such coated and/or treated fibers includes polyamide fibers coated with copper sulphide for an antistatic effect (for example R-STAT® from Rhodia) or another polymer allowing a particular organization of the fibers (specific surface treatment) or a surface treatment which induces colour/hologram effects (Lurexe® fiber from Sildorex, for example). Of course, mixtures of any of the fibers mentioned herein may also be used.

Depending on their properties, the fibers used according to the present invention may be introduced into or present in, e.g., an aqueous medium, an oily medium or a powder.

The fibers according to the invention are preferably chosen from polyamide fibers, poly(p-phenyleneterephthalamide) fibers and cotton fibers, and mixtures thereof. Their length preferably ranges from 0.1 mm to 10 mm, more preferably from 0.1 mm to 5 mm, and their average diameter can preferably range from 5 µm to 50 µm, and the shape factor preferably ranges from 5 to 150.

In particular, the polyamide fibers sold by Etablissements P. Bonte under the name Polyamide 0.9 Dtex can be used, having an average diameter of 15 µm to 20 µm, a yarn count of about 0.9 dtex (0.81 denier) and a length ranging from 0.3 mm to 5 mm (Polyamide 0.9 Dtex 0.3 mm, Polyamide 0.9 Dtex 3 mm or Polyamide 0.9 Dtex 5 mm). Poly(p-phenyleneterephthalamide) fibers with an average diameter of 12 µm and a length of about 1.5 mm can also be used, such as those sold under the name Kevlar Floc by the company Du Pont Fibers. These polyamide fibers are preferably introduced into an oily medium.

Cotton fibers such as those with a mean diameter of 20 µm, a length of from 0.3 mm and a shape factor of 15 may also be used.

The amount of fibers in the composition according to the invention is not limited and may vary within a wide range depending on the specific application and the type of product envisaged. It may preferably range, for example, from 0.1% to 50% by weight, preferably from 0.5% to 30% by weight and better still from 2% to 15% by weight relative to the total weight of the composition. For a make-up product for the face such as a foundation, or for the lips (such as a lipstick), the fiber concentration may preferably range from 0.1% to 20% of the total weight of the composition and more preferably from 0.5% to 10% of the total weight of the composition. For a special effect, especially for making up the body, the nails or the hair or for a care product for the face, the amount of fibers may be up to 30% of the total weight of the composition.

In the present specification the expression "copolymer comprising carboxylate groups and polydimethylsiloxane groups" means a copolymer obtained from (a) one or more carboxylic (acid or ester) monomers, and (b) one or more polydimethylsiloxane (PDMS) chains.

In the present application, the expression "carboxylic monomer" means both carboxylic acid monomers and carboxylic acid ester monomers. Thus, the monomer (a) may be chosen, for example, from acrylic acid, methacrylic acid, maleic acid, fumaric acid, itaconic acid and crotonic acid, esters thereof and mixtures of these monomers. Esters which may be mentioned include the following monomers: acrylate, methacrylate, maleate, fumarate, itaconate and/or crotonate. According to one preferred embodiment of the invention, the monomers in the form of esters are more particularly chosen from linear or branched, preferably $C_1$–$C_{24}$ and better still $C_1$–$C_{22}$, alkyl acrylates and methacrylates, the alkyl radical preferably being chosen from methyl, ethyl, stearyl, butyl, and 2-ethylhexyl radicals, and mixtures thereof.

Thus, according to one particular embodiment of the invention, the copolymer comprises as carboxylate groups at least one group chosen from acrylic acid, methacrylic acid and methyl, ethyl, stearyl, butyl or 2-ethylhexyl acrylate or methacrylate, and mixtures thereof.

In the present specification the term "polydimethylsiloxanes" (also referred to as polyorganosiloxanes or abbreviated as PDMS), in accordance with that which is generally accepted, means any organosilicon polymer or oligomer of linear structure, of variable molecular weight, and having a structure that would result from polymerization and/or polycondensation of suitably finctionalized silanes, and consisting essentially of a repetition of main units in which the silicon atoms are linked together via oxygen atoms (siloxane bond $\equiv$Si—O—Si$\equiv$), comprising methyl radicals directly linked via a carbon atom to the silicon atoms. The PDMS chains which may be used to obtain the copolymer used according to the invention comprise at least one polymerizable radical group, preferably located on at least one of the ends of the chain, that is to say that the PDMS may have, for example, a polymerizable radical group on both ends of the chain or may have a polymerizable radical group on one end of the chain and a trimethylsilyl end group on the other end of the chain. The polymerizable radical group may especially be an acrylic or methacrylic group, in particular a group $CH_2$=$CR_1$—CO—O—$R_2$, in which $R_1$ represents a hydrogen or a methyl group and $R_2$ represents —$CH_2$—, —$(CH_2)_n$— with n=3, 5, 8 or 10, $CH_2$—$CH(CH_3)$—$CH_2$—, —$CH_2$—$CH_2$—O—$CH_2$—$CH_2$—, —$CH_2$—$CH_2$—O—$CH_2$—$CH_2$—$CH(CH_3)$—$CH_2$—, —$CH_2$—$CH_2$—O—$CH_2CH_2$—O—$CH_2CH_2$—$CH_2$—.

The copolymers used in the composition of the invention may be obtained according to the usual methods of polymerization and grafting, for example by free-radical polymerization (A) of a PDMS comprising at least one polymerizable radical group (for example on one of the ends of the chain or on both of them) and (B) of at least one carboxylic monomer, as described, for example, in documents U.S. Pat. No. 5,061,481 and U.S. Pat. No. 5,219,560, both incorporated herein by reference.

The copolymers preferably have a weight average molecular weight ranging from about 3,000 to 200,000 and more preferably from about 5,000 to 100,000.

The copolymer used in the composition of the invention may be as is or in dispersed form in a solvent such as lower alcohols containing from 2 to 8 carbon atoms, for instance isopropyl alcohol, or oils, for instance volatile silicone oils (for example cyclopentasiloxane).

Copolymers includes in the composition of the invention are, for example, copolymers of acrylic acid and of stearyl acrylate with polydimethylsiloxane grafts, copolymers of stearyl methacrylate with polydimethylsiloxane grafts, copolymers of acrylic acid and of stearyl methacrylate with polydimethylsiloxane grafts, copolymers of methyl methacrylate, butyl methacrylate, 2-ethylhexyl acrylate and stearyl methacrylate with polydimethylsiloxane grafts. Mention may be made in particular, as a copolymer which may be used in the composition of the invention, of the copolymers sold by the company Shin-Etsu under the names KP-561 (CTFA name: acrylate/dimethicone), KP-541 in which the copolymer is dispersed to a proportion of 60% by weight in isopropyl alcohol (CTFA name: acrylate/dimethicone and isopropyl alcohol), KP-545 in which the copolymer is dispersed to a proportion of 30% in cyclopentasiloxane (CTFA name: acrylate/dimethicone and cyclopentasiloxane). According to one preferred embodiment of the invention, KP561 is preferably used; this copolymer is not dispersed in a solvent, but is in waxy form, its melting point being about 30° C.

The composition according to the invention may contain one or more of these copolymers. The amount of copolymer (s) is not limited. Preferably the copolymer may range, for example, from 0.01 to 20% by weight, preferably from 0.1% to 10% by weight and better still from 0.2% to 5% by weight relative to the total weight of the composition.

In a preferred embodiment, the physiologically acceptable medium of the composition of the invention comprises at least one oily phase. When the composition is in the form of an emulsion, this oily phase constitutes the oily phase of the emulsion.

The oily phase preferably contains at least one fatty substance chosen from volatile or non-volatile oils that are liquid at room temperature (20–25° C.), waxes, gums and pasty fatty substances, of animal, plant, mineral or synthetic origin, and mixtures thereof. The oily phase preferably contains at least one oil.

Oils useful in the composition of the invention include:

hydrocarbon-based oils of animal origin, such as perhydrosqualene;

hydrocarbon-based plant oils such as liquid triglycerides of fatty acids of 4 to 10 carbon atoms, such as heptanoic or octanoic acid triglycerides or alternatively, for example, sunflower oil, corn oil, soybean oil, marrow oil, grapeseed oil, sesame oil, hazelnut oil, apricot oil, macadamia oil, arara oil, castor oil, avocado oil, caprylic/capric acid triglycerides such as those sold by the company Stearineries Dubois or those sold under the names Miglyol 810, 812 and 818 by the company Dynamit Nobel, jojoba oil or Karite butter;

synthetic esters and ethers in particular of fatty acids, such as the oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate, and fatty alkyl heptanoates, octanoates and decanoates; polyol esters such as propylene glycol dioctanoate, neopentyl glycol diheptanoate or diethylene glycol diisononanoate; and pentaerythritol esters such as pentaerythrityl tetraisostearate;

linear or branched hydrocarbons of mineral or synthetic origin, such as volatile or non-volatile liquid paraffins and derivatives thereof, petroleum jelly, polydecenes or hydrogenated polyisobutene such as parleam oil;

fatty alcohols containing from 8 to 26 carbon atoms, such as cetyl alcohol, stearyl alcohol, and the mixture thereof (cetearyl alcohol), octyldodecanol, 2-butyloctanol, 2-hexyldecanol, 2-undecylpentadecanol or oleyl alcohol;

partially hydrocarbon-based and/or silicone-based fluoro oils such as those described in document JP-A-2 295 912 (incorporated herein by reference);

silicone oils such as volatile or non-volatile polydimethylsiloxanes (PDMSs) containing a linear or cyclic silicone chain, which are liquid or pasty at room temperature, in particular cyclopolydimethylsiloxanes (cyclomethicones) such as cyclopentasiloxane; polydimethylsiloxanes comprising alkyl, alkoxy or phenyl groups, pendant or at the end of a silicone chain, these groups containing from 2 to 24 carbon atoms; phenylsilicones such as phenyl trimethicones, phenyl dimethicones, phenyltrimethylsiloxydiphenylsiloxanes, diphenyl dimethicones, diphenylmethyldiphenyltrisiloxanes, 2-phenylethyl trimethylsiloxysilicates and polymethylphenylsiloxanes;

mixtures thereof.

Other fatty substances which may be present in the oily phase include, for example, fatty acids containing from 8 to 30 carbon atoms, for instance stearic acid, lauric acid or palmitic acid; waxes, for example lanolin, beeswax, carnauba wax, candelilla wax, paraffin wax, lignite wax or microcrystalline waxes, cerasin or ozokerite, synthetic waxes, for instance polyethylene waxes and Fischer-Tropsch waxes; gums such as silicone gums (dimethiconol); silicone resins such as trifluoromethyl-C1–4-alkyldimethicone and trifluoropropyldimethicone, and silicone elastomers, for instance the products sold under the names "KSG" by the company Shin-Etsu, under the name "Trefil" by the company Dow Corning or under the names "Gransil" by the company Grant Industries.

These substances may be chosen in a varied manner by a person skilled in the art in order to prepare a composition having the desired properties, for example consistency or texture properties.

The amount of oily phase in the composition of the invention is not limited, and may range from 0.55 to 99.89% of the total weight of the composition, preferably from 2% to 80% and better still from 5% to 70%.

The oily phase of the composition of the invention may optionally contain one or more lipophilic gelling agents. These lipophilic gelling agents (or thickeners) include, for example, modified clays such as modified magnesium silicate (bentone gel VS38 from Rheox), hectorite modified with distearyldimethyl-ammonium chloride (CTFA name: disteardimonium hectorite) sold under the name "bentone 38 CE" by the company Rheox. The lipophilic thickeners may be present in a proportion of, e.g., from 0% to 30% of the total weight of the composition and preferably 0.5% to 20%.

In addition, the composition of the invention may optionally contain an aqueous phase. Advantageously, the aqueous phase contains water and optionally one or more compounds that are at least partly miscible with water, for instance polyols, $C_2$ to $C_8$ lower monoalcohols, such as ethanol, and $C_3$ to $C_4$ ketones that are liquid at room temperature. The term "room temperature" should be understood as meaning a temperature of about (±5° C.) 25° C., at standard atmospheric pressure (760 mmHg).

The term "polyol" should be understood as meaning any organic molecule comprising at least two free hydroxyl groups. Polyols which may be mentioned, for example, include glycerol, glycols, for instance butylene glycol, propylene glycol, isoprene glycol and polyethylene glycols, sorbitol and sugars, for instance glucose.

The aqueous phase may optionally contain one or more hydrophilic gelling agents. Hydrophilic gelling agents include, for example, polysaccharide gums and derivatives thereof (xanthan gum, carboxymethylhydroxypropylguar); proteins; acrylic and vinyl polymers, modified natural polymers, and mixtures thereof.

The aqueous phase is not limited, and may represent from 0% to 98% of the total weight of the composition, preferably from 10% to 95% and better still from 30% to 95%. When it is desired to prepare a stick, the composition preferably comprises no or virtually no aqueous phase (0% or less than 5% by weight).

The water-miscible compound(s), such as polyols and lower alcohols, similarly are not limited and may be present in an amount ranging from 0% to 30% of the total weight of the composition, especially from 0.1% to 30% and better still in an amount ranging from 1% to 20%.

The composition of the invention may also comprise any additional additive used or useful in the field under consideration, such as dyestuffs, for instance pigments, nacres, water-soluble or liposoluble colorants, antioxidants, essential oils, preserving agents, cosmetic or dermatological active agents, for instance emollients, moisturizers (glycerol), vitamins, essential fatty acids, lipophilic or hydrophilic sunscreens, neutralizers, fillers, pH regulators (base or acid), electrolytes (for instance magnesium sulphate or sodium chloride), and fragrances, and mixtures thereof. These additives may be present in the composition in the amounts usually used, and, for example, in a proportion of from 0% to 20% of the total weight of the composition, and better still from 0.1% to 10%. Needless to say, a person skilled in the art knows how to select the optional additional additives and/or the amount thereof such that the advantageous properties of the composition according to the invention are not or are not substantially adversely affected by the addition envisaged. In particular, these additives should not harm the homogeneity, stability or comfort of the composition.

According to one particular embodiment of the invention, the composition contains at least one filler and/or one lipophilic thickener (gelling agent).

Fillers useful herein include talc, mica, silica, boron nitride and spherical fillers. As spherical fillers, mention may be made, for example, of Nylon® powders such as Nylon-12 (Orgasol® sold by the company Atochem), polyethylene powders, Teflon®, optionally modified starch, copolymer microspheres, such as those sold under the names Expancel® by the company Nobel Industrie or Polytrap® sold by the company Dow Coming, silicone resin microbeads such as those sold by the company Toshiba under the name Tospearl®, and mixtures thereof. The fillers may be present in any amount, including in a proportion of from 0% to 35% and preferably 0.5% to 15% of the total weight of the composition.

According to one preferred embodiment of the invention, the composition contains at least one filler, preferably at least one spherical filler such as, especially, Nylon-12, since the addition of fillers and especially of spherical fillers improves the disintegration of the composition on the skin and thus makes it easier to deposit the product on the skin.

The composition of the invention may be in any form, including in the form of a paste, a solid, a more fluid or less fluid cream, or a lotion. It may be in the form of an oily or aqueous gel, an oil-in-water or water-in-oil or multiple (W/O/W or O/W/O) dispersion or emulsion, which may be fluid, rigid or soft, etc., optionally cast as a stick or a dish.

According to one preferred embodiment of the invention, the composition is in the form of an emulsion, and more particularly in the form of a W/O emulsion (aqueous phase dispersed in oily phase) or O/W emulsion (oily phase dispersed in aqueous phase).

When the composition is an emulsion, the oily phase usually contains one or more oils and optionally other fatty substances, as described above. The proportion of the oily phase of the emulsion is not limited and may range, for example, from 5% to 80% by weight and preferably from 5% to 50% by weight relative to the total weight of the composition. The emulsifiers and optionally the coemulsifiers used in the composition in emulsion form can be chosen from those conventionally used in cosmetics or dermatology. The emulsifier and optionally the coemulsifier are not limited in type or amount and are generally present in the composition in a proportion ranging from 0.3% to 30% by weight and preferably from 0.5% to 20% by weight relative to the total weight of the composition. The emulsion may also contain lipid vesicles.

The emulsions generally may contain at least one emulsifier chosen from amphoteric, anionic, cationic or nonionic emulsifiers, used alone or as a mixture. The emulsifiers are chosen in an appropriate manner as is within the skill of the artisan, depending on the emulsion to be obtained (W/O or O/W emulsion).

For the W/O emulsions, useful emulsifiers include dimethicone copolyols such as the mixture of cyclomethicone and of dimethicone copolyol, sold under the name "DC 5225 C" by the company Dow Coming, and alkyldimethicone copolyols such as the laurylmethicone copolyol sold under the name "Dow Coming 5200 Formulation Aid" by the company Dow Corning, cetyl dimethicone copolyol sold under the name Abil EM 90® by the company Goldschmidt and mixtures thereof.

For the O/W emulsions, useful emulsifiers include oxyalkylenated (more particularly polyoxyethylenated) fatty acid esters of glycerol, oxyalkylenated (more particularly oxyethylenated) fatty acid esters of sorbitan, oxyalkylenated (oxyethylenated and/or oxypropylenated) fatty acid esters, oxyalkylenated (oxyethylenated and/or oxypropylenated) fatty alcohol ethers, and sugar esters, for instance sucrose stearate, and mixtures thereof.

The composition of the invention may constitute a dermatological or cosmetic composition intended especially for caring for, treating, cleansing and making up keratin materials and especially the skin, the lips, the hair, the eyelashes and the nails of human beings.

Thus, the invention may constitute a composition for treating or caring for the skin (including the scalp), keratin fibers (hair, eyelashes or eyebrows), the nails or the lips, or an antisun or artificial tanning composition, or alternatively a cleansing or make-up removing product for the skin, the hair, the eyebrows or the eyelashes, a deodorant product or a fragrancing product. It may be generally uncoloured or faintly coloured, and it may optionally contain cosmetic or dermatological active agents. It may be used as a care base for the skin or the lips (lip balms for protecting the lips against the cold and/or the sun and/or the wind) or as a day or night care cream for facial and/or body skin. It may also be in the form of a treating or non-treating, colouring or non-colouring shampoo, or a conditioner product.

The composition according to the invention may also constitute a coloured cosmetic composition and especially a make-up product for the skin, in particular a foundation, a blusher, a face powder, an eyeshadow, a mascara, an eyeliner, a concealer stick, a nail varnish, a lipstick or a lip gloss, optionally having care or treating properties, or a body tattoo.

Thus, a subject of the invention is also the use of the composition as defined above, to, e.g., care for, treat, cleanse and/or make up keratin materials. The subject of the invention is also a cosmetic process for caring for or treating keratin materials, and especially the skin, the hair or the lips of human beings, comprising the application to these keratin materials of the composition, in particular cosmetic composition, as defined above. Amounts to be applied or used vary with the purpose and form of the invention, as does the focus of application and repetition of application, all of which are within the skill of the ordinary artisan in view of this disclosure. For example, the user can apply 0.1–10 g of composition to the skin once or more per day.

The composition according to the invention may be prepared according to methods that are common in the applications fields under consideration, and known to those of skilled in the art.

The invention is illustrated in greater detail in the non-limiting example which follows. The compounds are indicated, depending on the case, as their CTFA name or their chemical name, and the percentages are given on a weight basis, except where otherwise mentioned.

| Example: White cream (W/O emulsion) | |
|---|---|
| Phase A | |
| Trifluoropropyl dimethicone | 4% |
| Dimethicone/dimethiconol | 2.5% |
| Nylon-12 (Orgasol) | 1.5% |
| Disteardimonium hectorite | 3% |
| Polyamide fibers | 12% |

| -continued | | |
|---|---|---|
| Example: White cream (W/O emulsion) | | |
| (Polyamide 0.9 dtex, 0,3 mm-Société Paul Bonte) | | |
| Cyclopentasiloxane | | 7% |
| Phase B | | |
| Cyclopentasiloxane/dimethicone copolyol (DC-3225 C) | | 10% |
| Acrylates/dimethicone copolymer (KP-561) | | 0.6% |
| Fragrance | | 0.1% |
| Phase C | | |
| Sodium chloride | | 5% |
| Glycerol | | 0.3% |
| Ethanol | | 2.5% |
| Preserving agents | | 1% |
| Water | qs | 100% |

Procedure: The constituents of phase A without the Nylon-12 and the fibers are mixed together with stirring. Separately, the constituents of phase B without the fragrance are mixed together with heating (about 45 to 50° C.) and stirred for 45 minutes, then phase B is cooled to room temperature (about 20 to 25° C.) and the fragrance is added thereto. This phase B is poured into phase A with stirring, the Nylon-12 and the fibers are added thereto and the mixture is homogenized. Phase C is prepared by mixing together the various constituents with stirring, and it is incorporated portionwise with stirring into the mixture obtained above.

A white cream is obtained, in which the fibers are homogeneously distributed, and which feels soft when applied. This cream may be used, for example, to care for the skin. The deposit obtained is very homogeneous.

French patent application 0015741 filed Dec. 5, 2000, is incorporated herein by reference, as are all documents mentioned above. Where a range is stated, it includes all values and sub-ranges therebetween as if specifically written out.

What is claimed is:

1. A composition comprising fibers and at least one copolymer comprising carboxylate groups and polydimethylsiloxane groups.

2. The composition according to claim 1, wherein the fibers have a length (L,) ranging from 1 $\mu$m to 10 mm.

3. The composition according to claim 1, wherein the fibers have a cross section which is within a circle of diameter (D) ranging from 1 nm to 100 $\mu$m.

4. The composition according to claim 1, wherein the fibers have a shape factor (L/D) ranging from 5 to 150.

5. The composition according to claim 1, wherein the fibers have a yarn count ranging from 0.15 to 30 denier.

6. The composition according claim 1, wherein the fibers are selected from the group consisting of silk fiber, cotton fiber, cork fiber, sugar cane fiber, wool fiber, flax fiber, cellulose fiber, polyamide fiber, modified cellulose fiber, poly(p-phenyleneterephthalamide) fiber, acrylic fiber, polyolefin fiber, glass fiber, silica fiber, aramide fiber, carbon fiber, Teflon® fiber, insoluble collagen fiber, polyester fiber, polyvinyl chloride fiber or polyvinylidene chloride fiber, polyvinyl alcohol fiber, polyacrylonitrile fiber, chitosan fiber, polyurethane fiber, polyethylene phthalate fiber, fibers formed from a mixture of polymers, resorbable synthetic fibers, and mixtures thereof.

7. The composition according to claim 1, wherein the fibers are treated and/or coated.

8. The composition according to claim 1, wherein the fibers are fibers of synthetic origin.

9. The composition according to claim 1, wherein the fibers are selected from the group consisting of polyamide fibers, poly(p-phenylterephthalamide) fibers, cotton fibers, and mixtures thereof.

10. The composition according to claim 1, wherein the fibers are present in an amount ranging from 0.1% to 50% by weight relative to the total weight of the composition.

11. The composition according to claim 1, wherein the copolymer comprises repeating units formed from (a) one or more carboxylic monomers, and (b) one or more polydimethylsiloxane chains comprising at least one polymerizable radical group.

12. The composition according to claim 11, wherein the monomer (a) is selected from the group consisting of acrylic acid, methacrylic acid, maleic acid, fumaric acid, itaconic acid, crotonic acid, esters thereof, and mixtures thereof.

13. The composition according to claim 11, wherein the polymerizable radical group of the copolymer is selected from the group consisting of acrylic acid, methacrylic acid and methyl, ethyl, stearyl, butyl or 2-ethylhexyl acrylates or methacrylates, and mixtures thereof.

14. The composition according to claim 1, wherein the copolymer is obtained by free-radical polymerization of a polydimethylsiloxane comprising at least one polymerizable radical group and of at least one carboxylic monomer.

15. The composition according to claim 1, wherein the copolymer has a weight average molecular weight ranging from 5,000 to 200,000.

16. The composition according to claim 1, wherein the amount of copolymer ranges from 0.01% to 20% by weight of active material relative to the total weight of the composition.

17. The composition according to claim 1, further comprising an oily phase.

18. The composition according to claim 17, wherein the oily phase comprises at least one fatty substance selected from the group consisting of volatile and nonvolatile oils that are liquid at room temperature, waxes, gums, pasty fatty substances, and mixtures thereof.

19. The composition according to claim 1, further comprising an aqueous phase.

20. The composition according to claim 1, further comprising at least one filler and/or one lipophilic thickener.

21. The composition according to claim 1, further comprising at least one spherical filler.

22. The composition according to claim 1, in the form of an oily or aqueous gel, a oil-in-water emulsion, a water-in-oil emulsion, or a multiple emulsion.

23. The composition according to claim 1, in the form of a dermatological or cosmetic composition.

24. The composition according to claim 1, in the form of a treatment or care composition for the skin, keratin fibers, the nails or the lips, an antisun or artificial tanning composition, a cleansing or make-up-removing product for the skin, the hair, the eyebrows or the eyelashes, a deodorant product, a fragrancing product, a foundation, a blusher, a face powder, an eyeshadow, a mascara, an eyeliner, a concealer stick, a nail varnish, a lipstick or a lip gloss.

25. A method comprising applying the composition of claim 1 to a keratin material.

26. The method of claim 25, wherein said keratin material is keratin material of a human being.

27. The method of claim 26, wherein said keratin material of a human being is selected from the group consisting of skin, scalp, lips of the face, and integuments thereof.

28. A method for preparing a fiber-containing composition, comprising mixing together fibers and a copolymer comprising carboxylate groups and polydimethylsiloxane groups.

29. The composition according to claim 1, wherein the arboxylate group is acrylic acid.

30. The composition according to claim 1, wherein the polydimethylsiloxane group is dimethicone.

31. The composition according to claim 1, wherein the carboxylate group is acrylic acid and the polydimethylsiloxane group is dimethicone.

32. The composition according to claim 1, wherein the a amount of copolymer ranges from 0.2 to 5.0% by weight relative to the total weight of the composition.

33. The composition according to claim 29, wherein the mount of copolymer ranges from 0.2 to 5.0% by weight relative to the total weight of the composition.

34. The composition according to claim 30, wherein the mount of copolymer ranges from 0.2 to 5.0% by weight relative to the total weight of the composition.

35. The composition according to claim 31, wherein the mount of copolymer ranges from 0.2 to 5.0% by weight relative to the total weight of the composition.

36. The composition according to claim 1, wherein the a amount of fiber ranges from 2 to 15% by weight relative to the total weight of the composition.

37. The composition according to claim 33, wherein the amount of fiber ranges from 2 to 15% by weight relative to the total weight of the composition.

38. The composition according to claim 34, wherein the mount of fiber ranges from 2 to 15% by weight relative to the total weight of the composition.

39. The composition according to claim 35, wherein the mount of fiber ranges from 2 to 15% by weight relative to the total weight of the composition.

40. The composition according to claim 1, wherein the a amount of fiber ranges from 0.5 to 10% by weight relative to the total weight of the composition.

41. The composition according to claim 33, wherein the amount of fiber ranges from 0.5 to 10% by weight relative to the total weight of the composition.

42. The composition according to claim 34, wherein the amount of fiber ranges from 0.5 to 10% by weight relative to the total weight of the composition.

43. The composition according to claim 35, wherein the a amount of fiber ranges from 0.5 to 10% by weight relative to the total weight of the composition.

44. The composition according to claim 1, further comprising a dyestuff.

45. The composition according to claim 1, further comprising at least one pigment.

* * * * *

UNITED STATES PATENT AND TRADEMARK OFFICE
CERTIFICATE OF CORRECTION

PATENT NO. : 6,656,487 B2
DATED : December 2, 2003
INVENTOR(S) : Isabelle Afriat et al.

It is certified that error appears in the above-identified patent and that said Letters Patent is hereby corrected as shown below:

<u>Column 10,</u>
Line 52, "according claim" should read -- according to claim --.

<u>Column 12,</u>
Line 11, "arboxylate" should read -- carboxylate --;
Line 18, delete "a";
Lines 22, 25, 28, 38 and 41, "mount" should read -- amount --;
Lines 30 and 43, "the a" should read -- the --; and
Line 53, "a amount" should read -- amount --.

Signed and Sealed this

Thirteenth Day of April, 2004

JON W. DUDAS
*Acting Director of the United States Patent and Trademark Office*